US008865775B2

(12) United States Patent
Maeda et al.

(10) Patent No.: US 8,865,775 B2
(45) Date of Patent: Oct. 21, 2014

(54) ANTI-INFLAMMATORY AGENT AND CANCER-PREVENTIVE AGENT COMPRISING CANOLOL OR PRODRUG THEREOF AND PHARMACEUTICAL, COSMETIC AND FOOD COMPRISING THE SAME

(75) Inventors: Hiroshi Maeda, Kumamoto (JP); Tetsuya Tsukamoto, Nagoya (JP); Masae Tatematsu, Nagoya (JP)

(73) Assignee: Hiroshi Maeda, Kumamoto-Shi, Kumamoto (JP)

( * ) Notice: Subject to any disclaimer, the term of this patent is extended or adjusted under 35 U.S.C. 154(b) by 190 days.

(21) Appl. No.: 13/354,507

(22) Filed: Jan. 20, 2012

(65) Prior Publication Data
US 2012/0122995 A1    May 17, 2012

Related U.S. Application Data

(63) Continuation of application No. 12/294,972, filed as application No. PCT/EP2004/013197 on Nov. 20, 2004, now abandoned.

(51) Int. Cl.
| | |
|---|---|
| *A01N 31/14* | (2006.01) |
| *A61K 31/075* | (2006.01) |
| *C07C 41/00* | (2006.01) |
| *C07C 43/02* | (2006.01) |
| *C07C 43/20* | (2006.01) |
| *A61K 31/09* | (2006.01) |

(52) U.S. Cl.
CPC .................................. *A61K 31/09* (2013.01)
USPC ........................................ 514/720; 568/658

(58) Field of Classification Search
USPC ........................................ 514/720; 568/658
See application file for complete search history.

(56) References Cited

U.S. PATENT DOCUMENTS

2005/0042354 A1    2/2005  Morimura et al. ............ 426/601

FOREIGN PATENT DOCUMENTS

| EP | 1440687 A1 | 7/2004 |
| JP | WO 03/030888 | 4/2003 |
| WO | WO2007095588 A1 | 8/2007 |

OTHER PUBLICATIONS

Franco et. al., Prostaglandins and other Lipid Mediators, 1999, Elsevier, vol. 58, pp. 9-17.*
Kubo et. al., Bioorganic and Medicinal Chemistry Letters, 2002, Pergamon, vol. 12, pp. 113-116.*
Robinson et. al., Journal of Medicinal Chemistry, 1996, American Chemical Society, vol. 39, pp. 10-18.*

Al-Marhoon et al. "cagA+ *Helicobacter pylori* Induces Greater Levels of Prostaglandin $E_2$ than cagA- Strains" Prostaglandins & other Lipid Mediators 2004 73:181-189.
Fukui et al. "*Helicobacter pylori*" G. I. Research 1997 5(5):14-19 with translation.
Gambero et al. "Acute Inflammatory Response Induced by *Helicobacter pylori* in the Rat Air Pouch" FEMS Immunology and Medical Microbiology 2003 38:193-198.
Cao et al., Earlier *Helicobacter pylori* Infection Increases the Risk for the N-Methyl-N-nitrosourea-induced Stomach Carcinogenesis in Mongolian Gerbils, Jpn. J. Cancer Res. 2002 93:1293-1298.
Cao et al., "4-Vinyl-2,6-dimethoxyphenol (canolol) suppresses oxidative stress and gastric carcinogenesis in *Helicobacter pylori*-infected carcinogen-treated Mongolian gerbils", Int. J. Cancer 2008 122:1445-1454.
Jolad et al., "Commercially processed dry ginger (Zingiber officinale):Composition and effects on LPS-stimulated $PGE_2$ production", Phytochemistry 2005 66:1614-1635.
Kanazawa et al., "Dietary lipid peroxidation products and DNA damage in colon carcinogenesis", Eur. J. Lipid Sci. Technol. 2002 104:439-447.
Kundu et al., "Breaking the relay in deregulated cellular signal transduction as a rationale for chemoprevention with anti-inflammatory phytochemicals", Mutation Research 2005 591:123-146.
Kuwahara et al., "Antioxidative and Antimutagenic Activities of 4-Vinyl-2,6-dimethoxyphenol (Canolol) Isolated from Canola Oil" J. Agric. Food. Chem. 2004 52:4380-4387.
Sawa et al., "Lipid Peroxyl Radicals from Oxidized Oils and Heme-Iron:Implication of a High-Fat Diet in Colon Carcinogenesis", Cancer Epidemiology, Biomarkers & Prevention 1998 7:1007-1012.
Shimizu et al., "Eradication Diminishes Enhancing Effects of *Helicobacter pylori* Infection on Glandular Stomach Carcinogenesis in Mongolian Gerbils", Cancer Research 2000 60:1512-1514.
Stuehr et al., "Nitric Oxide", J. Exp. Med. 1989 169:1543-1555.
Vuorela et al., "Preclinical Evaluation of Rapeseed, Raspberry, and Pine Bark Phenolics for Health Related Effects", J. Agric. Food Chem. 2005 53:5922-5931.
Wakamatsu et al., "Isolation, Identification, and Structure of a Potent Alkyl-Peroxyl Radical Scavenger in Crude Canola Oil, Canolol", Biosci. Biotechnol. Biochem. 2005 69(8):1568-1574.
Vuorela et al. "Effect of Plant Phenolics on Protein and Lipid Oxidation in Cooked Pork Meat Patties" Journal of Agricultural and Food Chemistry 2005 vol. 53: 8492-8497.
Kuwahara et al. "Antioxidative and Antimutagenic Activities of 4-Vinyl-2, 6-Dimethoxyphenol (Canolol) Isolated from Canola Oil" Journal of Agricultural and Food Chemistry 2004 vol. 52: 4380-4387.
Extended European Search Report issued in EPO Application 06730565.6, Mar. 18, 2010, EPO.
Song, et al., Bioorganic & Medicinal Chemistry Letters, 2003. Pergamon, vol. 13. pp. 297-300.
Surh, Nature Rev. Cancer, 2003, Nature Publishing Group, vol. 3 pp. 768-780.
Cuzick et al., The Lancet, 2003, The Lancet Publishing Group, vol. 361, pp. 296-300.

* cited by examiner

*Primary Examiner* — Sarah Pihonak
(74) *Attorney, Agent, or Firm* — Licata & Tyrrell P.C.

(57) ABSTRACT

An anti-inflammatory agent or cancer-preventive agent comprising 4-vinyl-2,6-dimethoxyphenol of the formula (1): or a PD thereof.

7 Claims, 5 Drawing Sheets

Figure 1
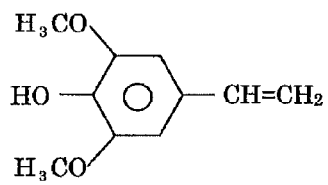
Figure 2  Microscopic image
 
          Group A                          Group B
    0.1% canolol / 0.5 ppm BHT / AIN93G        0.5 ppm BHT / AIN93G Group A  
0.1% canolol / 0.5 ppm BHT / AIN93G Group B  
0.5 ppm BHT / AIN93G Group A  
0.1% canolol / 0.5 ppm BHT / AIN93G Group B  
0.5 ppm BHT / AIN93G (iNOS immunohistochemistry, 200×)

Figure 4 Activation of macrophages
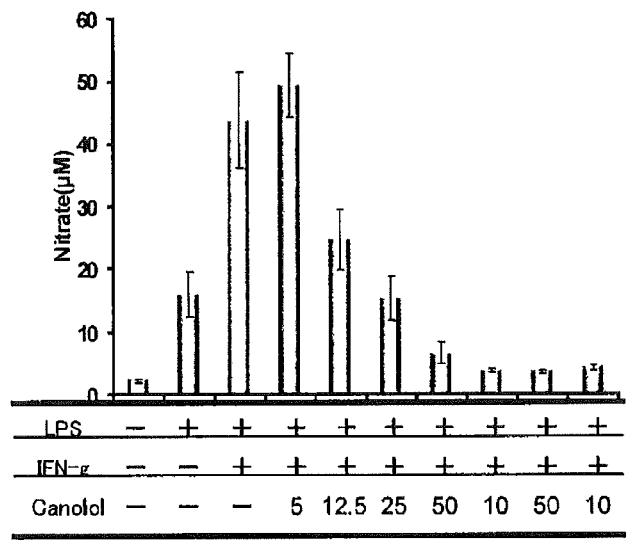
Figure 5 Cytotoxicity test against macrophages
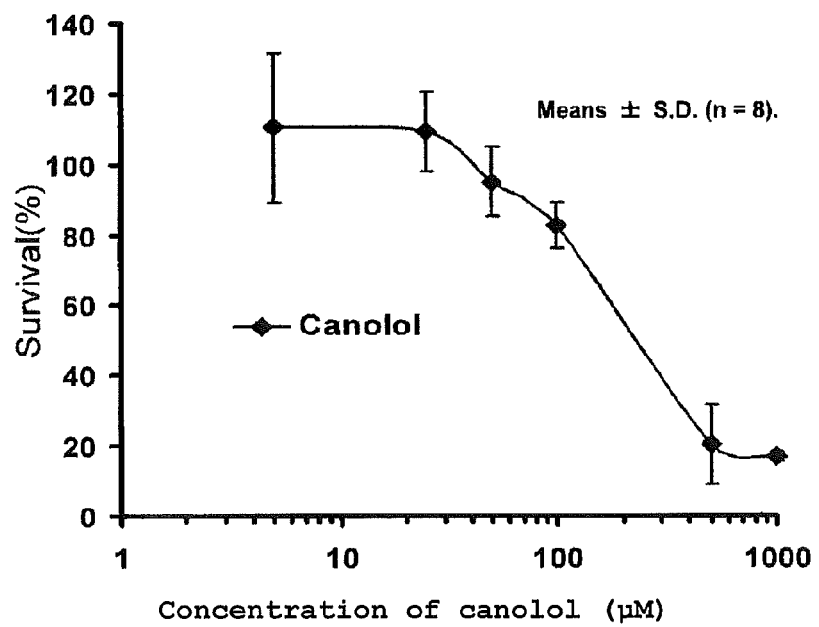

Figure 6  Protective effects of canolol on the cytotoxicity by ONOO⁻ in human embryonic kidney cell 293
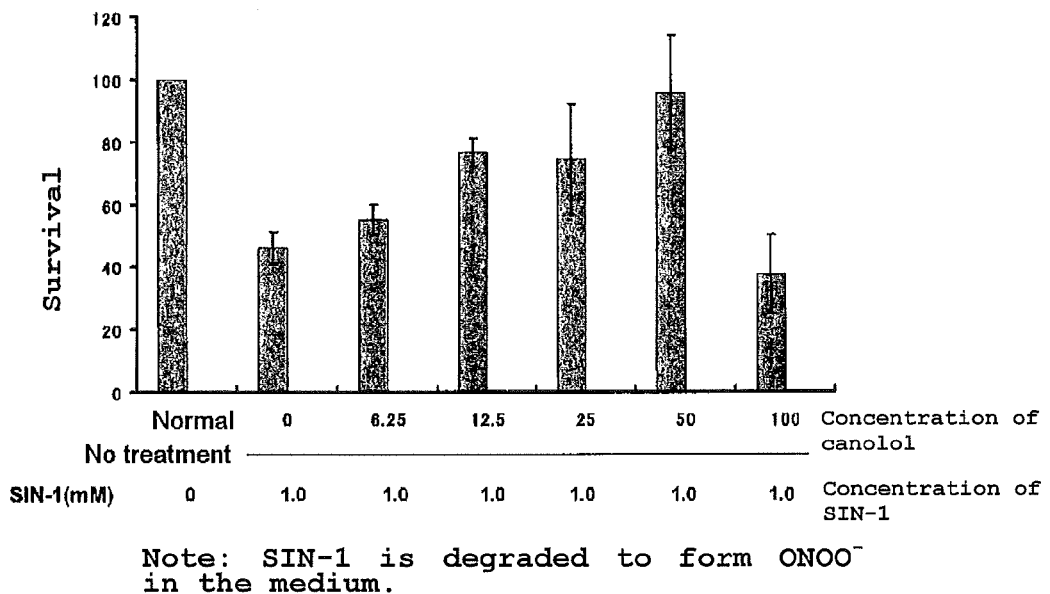
Note: SIN-1 is degraded to form ONOO⁻ in the medium.
Figure 7A
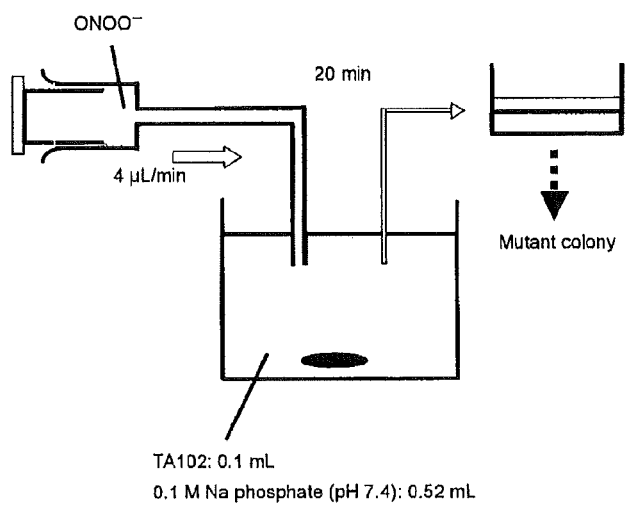

ANTI-INFLAMMATORY AGENT AND CANCER-PREVENTIVE AGENT COMPRISING CANOLOL OR PRODRUG THEREOF AND PHARMACEUTICAL, COSMETIC AND FOOD COMPRISING THE SAME

INTRODUCTION

This patent application is a continuation of U.S. patent application Ser. No. 12/294,972, filed Dec. 31, 2008, now abandoned which is the National Stage of International Application No. PCT/JP2006/306617, filed Mar. 30, 2006, the teachings of which are incorporated herein by reference in their entireties.

BACKGROUND ART

An anti-inflammatory agent is a substance that suppresses inflammatory cytokines and/or inflammatory mediators (such as prostaglandins). Aspirin and teprenone are known examples of anti-inflammatory agents.

A cancer-preventive agent is a substance that prevents carcinogenesis induced by intake of carcinogen or by chronic infection. No remarkable agent has been known so far. Under these circumstances, the inventors investigated agents from various crude oils or fats from various plant seeds that neutralize lipid-peroxyl radicals (hereinafter "LOO●"), which exhibits, for example, strand breaks of DNA and cytotoxicity, and found an aromatic compound named canolol (4-vinyl-2,6-dimethoxyphenol, FIG. 1) from crude canola (rape seed) oil (T. Sawa et al, Cancer Epidemiology, Biomarkers & Prevention, 7, 1007-1012 (1998); H. Kuwahara et al, J. Agric. Food Chem., 52, 4380-4387 (2004); D. Wakamatsu et al, Biosci., Biotech., Biochem., 69, 1568-1574 (2005); A. Kanazawa et al, Eur. J. Lipid Science Tech., 104, 439-447 (2002); WO 2003/030888).

The present inventors demonstrated that canolol could effectively scavenges LOO● that are toxic to the host.

Since canolol has LOO● neutralizing activity, it may be used as a medicament, cosmetic, or food ingredient.

DISCLOSURE OF THE INVENTION

However, there is no existing knowledge that canolol or PD thereof can be used as such an ingredient and results in desired effects. Because canolol is not widely known, and that it is not commercially available, there has been no medicament, cosmetic or food additive containing canolol as an active ingredient.

Further, among existing anti-inflammatory agents or cancer-preventive agents, there has not been any satisfactory compound in view of their performance and side effect. Therefore there is a strong demand to develop better anti-inflammatory agents and cancer-preventive agents.

Means of Solving the Problem

Under such circumstances, the present inventors undertook research to develop canolol applications to solve the above problem, and have found that canolol possesses potent therapeutic or prophylactic effects on inflammation and cancer, and by investigating further, the present invention has thus been accomplished. More specifically, the present inventors examined preventive effects on gastric cancer development using Mongolian gerbils which were infected with *Helicobacter pylori* as a model of chronic inflammation, and have found that administration of canolol strongly suppressed stomach and duodenum inflammation; the present invention has thus been accomplished.

Namely, the present invention relates to (1) 4-vinyl-2,6-dimethoxyphenol.

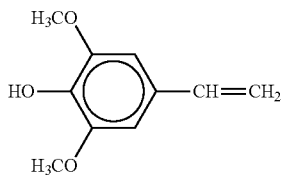

(2) In addition, the present invention relates to said anti-inflammatory agent for treatment of one or two of the following diseases: gastro-duodenitis, gastro-duodenal ulcer, gastritis, bronchitis, rheumatism, hepatitis, colitis, conjunctivitis, pneumonitis, pancreatitis, stomatitis, pharyngitis and burn.

(3) Furthermore, the present invention relates to said anti-inflammatory agent, wherein inflammation is suppressed by one or more of the followings: suppression of 8-oxodeoxyguanosine formation, inhibition of COX-2 activity, inhibition of nitric oxide synthase (iNOS) activity and suppression of NO production.

(4) In addition, the present invention relates to said cancer-preventive agent, wherein carcinogenesis is prevented by suppression of mutagenesis by peroxynitrite.

(5) Furthermore, the present invention relates to said anti-inflammatory agent or cancer-preventive agent (medicament), further comprising an excipient for medicament.

(6) In addition, the present invention relates to said anti-inflammatory agent or cancer-preventive agent (cosmetic), further comprising a cosmetic ingredient (cosmetic component).

(7) Furthermore, the present invention relates to said anti-inflammatory agent or cancer-preventive agent for treatment of one or more of the following symptoms: aging of skin, cytotoxicity and sunburn.

(8) In addition, the present invention relates to said anti-inflammatory agent or cancer-preventive agent (medicament or cosmetic) in the form of cream, tablet, capsule, lipid formulation, aqueous formulation (water solubilized form) or in emulsion.

(9) Furthermore, the present invention relates to said anti-inflammatory agent or cancer-preventive agent, further comprising a food ingredient.

In the past, there has not been any established knowledge with respect to relationship between treatment of inflammation or prevention of cancer and neutralization of LOO●. Also, there has not been any established practical usage of canolol as described above. Notwithstanding such a background, the present invention has accomplished to provide an anti-inflammatory agent and cancer-preventive agent by utilizing canolol's LOO●. neutralizing activity. In addition, the present invention provides a cosmetic and food with cancer preventing activity.

Effects of the Invention

The present invention provides an anti-inflammatory agent and cancer-preventive agent with sufficient anti-inflammatory and cancer preventive activity while having less side effect, and further provides medicament, cosmetic and food comprising said agents. The active component used in the present invention is canolol, an active ingredient according to the invention has the following advantages:

(1) It is lipid soluble (lipophilic) and has a potent antiradical activity.

(2) Because of its lipophilicity, canolol has high affinity with cell membranes in vivo, namely, it acts effectively in the lipid-rich cell membranes and organs where a hydrophilic antiradical agent cannot easily fit.

(3) Because it is a natural ingredient obtained from the extract of edible rape seed crude oil, it is safe and has abundant resources, and because of its relatively simple structure, it can be easily synthesized.

(4) Compared to existing antioxidants obtained from defatted rape seed residue, which is insoluble in lipid, canolol is obtained from rape seed oil (canola oil) and is lipid soluble and thus it is possible to apply it as an antioxidant for edible oil or in lipid compositions.

Therefore, the anti-inflammatory agent and cancer-preventive agent according to the invention, and the medicament, cosmetic or food comprising the same exert superior effects in terms of manufacture, manufacturing cost, bioactivity, safety, administration and intake.

In addition, among the anti-inflammatory agents of the invention, those which may be used for treatment of one or more of the following diseases: gastro-duodenitis, gastro-duodenal ulcer, gastritis, bronchitis, rheumatism, hepatitis, colitis, conjunctivitis, pneumonitis, pancreatitis, stomatitis, pharyngitis and burn, can be used for treatment of a wide variety of other inflammatory diseases.

Furthermore, among the anti-inflammatory agents of the invention, those which suppress inflammation by one or more selected from: suppression of 8-oxodeoxyguanosine formation, inhibition of COX-2 activity, inhibition of iNOS activity (suppression of NO production) and inhibition of cytokine induction, have various mechanism of action and can be used for treatment of a wide variety of inflammation [a reference related to suppression of cytokine production by phytochemicals such as flavonoids: J. K. Kundu, Y. J. Surh, Mutation Res. 591, 123-146(2005)].

In addition, among the cancer-preventive agents of the invention, those which prevents carcinogenesis by suppression of mutagenesis by peroxynitrite exhibit effects as cancer-preventive agents.

Also, among the anti-inflammatory agents or cancer-preventive agents, those which comprise an excipient for medicament (medicaments) exhibit effects that they facilitate treatment of diseases.

In addition, among the anti-inflammatory agents or cancer-preventive agents, those which further comprise a cosmetic ingredient are used as cosmetics and exhibit anti-inflammatory activity and/or cancer preventive effects.

Furthermore, among the anti-inflammatory agents or cancer-preventive agents comprising a cosmetic ingredient, those which are used for treatment of one or more of the following symptoms: aging of skin, cytotoxicity and sunburn, exhibit effects that they facilitate treatment of various inflammation by employing a treatment means that is similar to application of conventional cosmetics.

In addition, among the anti-inflammatory agents or cancer-preventive agents of the invention, those which have the form of cream, tablet, capsule, lipid formulation, aqueous formulation (water solubilized form) or emulsion exhibit effects that they further facilitate treatment of diseases.

Furthermore, among the anti-inflammatory agents or cancer-preventive agents of the invention, those which further comprise a food ingredient are taken like conventional foods and exhibit anti-inflammatory activity and/or cancer preventive effects.

BRIEF DESCRIPTION OF THE DRAWINGS

FIG. 1 shows the chemical structure of canolol.

FIG. 2 shows anti-inflammatory activity of the anti-inflammatory agent of the invention.

FIG. 4 shows suppression of NO production from macrophage by treatment with the anti-inflammatory agent of the invention.

FIG. 5 shows the effects of the anti-inflammatory agent of the invention on the viability of macrophages.

FIG. 6 shows the effects of the cancer-preventive agent of the invention on genetic damage by $ONOO^-$.

FIG. 7A shows colonies under constant flux of $ONOO^-$ infusion under constant mixing.

BEST EMBODIMENT OF THE INVENTION

Figure 3A:
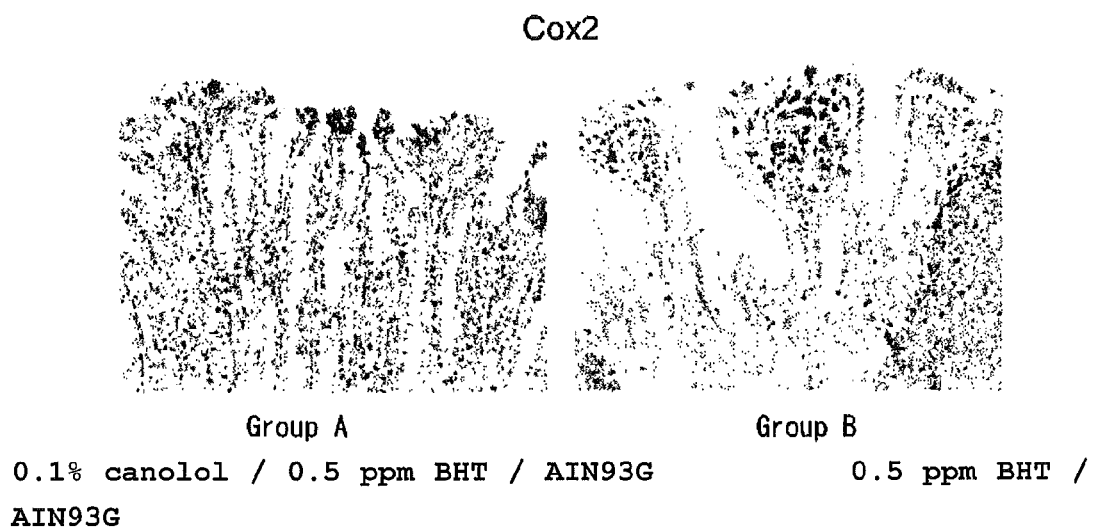
FIG. 3A shows pathological findings of COX-2 after immunostaining.

The anti-inflammatory agent and the cancer-preventive agent of the invention and medicament, cosmetics or food comprising the same may be in any composition or form as far as they comprise canolol or PD thereof. Canolol or PD thereof can be obtained by extraction from rape seed oil as described in, for example WO 2003/030888. Canolol can also be chemically synthesized from sinapic acid (3,5-dimethoxy-4-hydroxycinnamic acid) or phenol by a known procedure.

The amount of canolol in these anti-inflammatory agent and cancer-preventive agent comprising canolol or PD thereof and medicament, or cosmetic or food comprising the same may be modified according to purposes. For example, as a anti-inflammatory agent, various formulations comprising 0.1-5% of canolol or PD thereof are preferred, various formulations comprising 0.1-3% of canolol or PD thereof are more preferred.

The anti-inflammatory agent of the invention may further comprise an additional component such as camphor, sucralfate, methyl salicylate and teprenone. Teprenone is preferred.

The anti-inflammatory agent of the invention exerts anti-inflammatory effects on various types of inflammation. Examples of inflammation are one or more selected from: gastro-duodenitis, gastro-duodenal ulcer, gastritis, bronchitis, rheumatism, hepatitis, colitis, conjunctivitis, pneumonitis, pancreatitis, stomatitis, pharyngitis and burn. More specifically, since the anti-inflammatory agent of the invention exhibits superior effects on gastro-duodenitis, it is preferably used for these inflammations.

The cancer preventive agent of the invention may comprise an additional ingredient such as sucralfate and teprenone.

The cancer-preventive agent of the invention exhibits preventive activity against various cancers. Examples of cancers include one or more from: gastric cancer, colon cancer, hepatoma, gallbladder cancer, bile duct cancer, oesophageal cancer and lung cancer.

Since the cancer-preventive agent of the invention exhibits superior effects particularly on prevention of gastric cancer development, it is preferably used for these cancers.

The anti-inflammatory agent or cancer-preventive agent of the invention may comprise a conventional supplemental ingredient such as water, organic solvent, emulsifier, oil and fat. Other components may be modified according to purposes.

A pharmaceutical component comprising the anti-inflammatory agent or cancer-preventive agent of the invention, namely, medicament, is the anti-inflammatory agent or cancer-preventive agent comprising canolol or PD thereof as an active ingredient, and can be used for human or veterinary medicine. The excipient for medicament suitable for formulation of medicament of the invention is suitable for enteral (e.g., oral route), parenteral or topical administration, and is an organic or inorganic substance, which does not react with said compound, for example water, vegetable oil, benzyl alcohol, alkylene glycol, polyethylene glycol, glycerol triacetate, gelatin, carbohydrate such as lactose and starch, magnesium stearate, talc and vaseline (petrolatum).

Formulations suitable for oral administration are tablet, pill, coated tablet, capsule, powder, granule, syrup, juice, solution, suspension or drop; formulations suitable for rectal administration are suppository; formulations suitable for parenteral administration are solution, preferably oil-based solution, aqueous solution, suspension, emulsion or implant; and formulations suitable for topical application are ointment, cream, or powder, or patch for transdermal application.

As an administration form of medicament of the invention, oral administration is preferred because canolol exhibits its activity by oral administration and in terms of easiness in administration. Since said oral administration can be performed by the subject itself, it is also beneficial in terms of improvement of compliance, such as saving inconvenience of visiting clinic.

Canolol and PD thereof are relatively heat-stable, thus sterilization can be performed during manufacturing of the injectable formulation, and/or auxiliaries such as lubricant and preservative and/or moistening agent, emulsifier, PD to change osmotic pressure, buffering agent, coloring agent and flavoring agent and/or other active ingredients such as one or more vitamins may be added.

Formulations suitable for administration in the form of aerosol or spray are, for example, solution, suspension or emulsion of the pharmaceutically acceptable active ingredient represented by formula (1).

In general, the medicament of the invention is administrated per unit dose at 1-500 mg per kg body weight as the amount of active ingredient, more preferably 5-100 mg per kg body weight. Daily dose is about 0.01-100 mg per kg body weight, more preferably about 0.1-80 mg, particularly preferably about 1-70 mg/kg. However, specific dose to each individual patient may be variable depending on a wide range of factors, for example, efficacy of the specific compound employed, age, body weight, general health condition, sex, dietary interval, timing and method of administration, excretion rate, combination with other drugs, and severity of the diseases. Amongst all, oral administration is preferred.

Accordingly, the invention further relates to use of the medicaments for manufacturing, particularly by non-chemical procedure. In this case, the active ingredients of these medicaments, canolol and PD thereof may be formulated in a suitable dosage form with at least one solid, liquid and/or semi-liquid excipient or auxiliary, and if desired in combination with one or more other active ingredients.

In addition to the anti-inflammatory agent or cancer-preventive agent of the invention, compositions comprising cosmetic ingredients, namely, cosmetics, have anti-inflammatory activity against various inflammations and/or cosmetic effects. Examples of inflammations include one or more selected from aging of skin, cytotoxicity and sun burn. Since the cosmetics of the invention exhibit superior effects on prevention of inflammations particularly caused by sun, or ultraviolet ray, these cosmetics are preferably used for such inflammations.

The term "prodrug" (hereinafter "PD") used herein means a drug that it is inactive as PD per se, but it becomes active only after it is chemically reacted by drug metabolizing enzymes in vivo. PD of canolol used for the invention is not limited, but PD represented by the following formula is exemplified:

[Chem. 2]

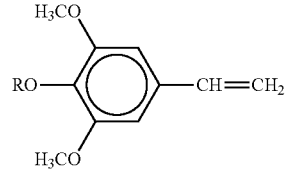

(wherein R is a carboxyl residue having 1-24 carbon atoms).

R is preferably fatty acid residue having 1-24 carbon atoms, amino acid residue, peptide spacer, sugar residue or organic acid residue, more preferably, $CH_3CO-$, $C_2H_5CO-$, $NH_2CH_2CO-$, $NH_2CH(R')CO-$ (wherein R' is amino acid side-chain residue).

An example of preferred peptide spacers are Gly-Phe-Len-Gly.

Preferred examples of sugar residues are those of sugars, such as glucuronic acid, uronic acid, ascorbic acid, sialic acid and hyaluronic acid. Preferred examples of organic acid residues are those of organic acids, such as malic acid, citric acid, oxalic acid, malonic acid and succinic acid.

Such bonds as ester bond or amide bond with acyl group or peptide spacer are hydrolyzed by esterases, amidases, cathepsins or peptidases, and yield parental drug, canolol.

According to the invention, PD is preferred to deliver canolol to the target site more efficiently and to prepare lipophilic formulations more easily.

The cosmetic of the invention may comprise additional ingredients, e.g. carotenes such as β-carotene, tocopherol, vitamin C or its derivative, melanin, chlorophyll, lignin, phytic acid, kojic acid and BHT (butyl hydroxyl toluene). β-carotene and/or tocopherol is most preferred.

Such cosmetic ingredients include excipients, fragrances, coloring agents and other active ingredients.

The excipients include lipids such as olive oil, honey wax, lanolin, candelilla wax, squalene, paraffin, stearic acid, cetanol (cetyl alcohol), octyldodecyl myristate, tri(caprylcapric acid) and glycerin; water soluble synthetic polymers such as sodium alginate, dextrin, sodium carboxymethylcellulose, carboxyvinylpolymer and polyvinylalcohol; polyalcohols such as propyleneglycol and polyethylene glycol; sugars such as glucose, sorbitol and maltitol; surfactants such as sorbitan monostearate, polyoxyethylene glyceryl monostearate and polyoxyethylene nonylphenylether. These excipients may be used alone or in combination of two or more.

One or more flagrances may be recommended as embodiments of the invention to enhance consumers' preference. Either natural or synthetic flavors may be used according to the invention. For example, one or plural plant and/or fruit flavors may be used, and such flavors may be either synthetic or natural flavors, preferably combination thereof.

Flagrances include a mixture of various flavors. If desired, flavors in fragrances may be in the form of emulsified droplets, which may be dispersed in drinks or concentrates. Typically, the fragrances are available as concentrates or as extracts, or in the form of synthetically produced flavor esters, alcohols, aldehydes, terpenes or sesquiterpenes.

The coloring agents are, for example, tar pigments such as "Red No. 2" and "Blue No. 1" and inorganic dyes such as talc, mica and titanium oxide.

Said other active ingredients may be selected according to cosmetic uses, and include vitamins such as vitamin E, vitamin C and vitamin ID; animal or plant extracts such as licorice, aloe and placenta; antioxidants such as dibutylhydroxytoluene; and antiplasmin agents such as ε-aminocapronic acid and tranexamic acid; and ultraviolet absorbers such as para-methoxycinnamic acid ethylhexyl ester and oxybenzone.

The amount of each cosmetic ingredient is variable, and it is preferred to adjust according to the purposes.

Examples of the forms of the cosmetics of the invention include the forms of cream, tablet, capsule, lipid formulation or aqueous formulation (water solubilized form) or emulsion.

In addition to the anti-inflammatory agents and cancer-preventive agents of the invention, compositions comprising various food ingredients, namely foods, exert anticarcinogenesis activity or anti-inflammatory activity. Also, the food of the invention comprises, in addition to canolol, at least one food ingredient such as protein, carbohydrate, fat, vitamins and minerals.

Non-limiting examples of vitamins and minerals include niacin, thiamine, folic acid, pantothenic acid, biotin, vitamin A, vitamin C, vitamin $B_2$, vitamin $B_3$, vitamin $B_6$, vitamin $B_{12}$, vitamin D, vitamin E, vitamin K, iron, zinc, copper, phosphorous, iodine, chromium, molybdenum and fluorine. More preferably, in case that vitamins or minerals are used, they are selected from niacin, thiamine, folic acid, iodine, vitamin A, vitamin C, vitamin $B_6$, vitamin $B_{12}$, vitamin D, vitamin E, iron, zinc and calcium. Preferably, at least one vitamin is selected from vitamin C, vitamin $B_6$, vitamin $B_{12}$, vitamin E, pantothenic acid, niacin and biotin. Preferably, the compositions of the invention comprise one or plural of other vitamins selected from vitamin C and vitamin $B_6$, vitamin $B_{12}$, vitamin E, pantothenic acid, niacin and biotin.

Foods of the invention may comprise an effective amount of one or plural sweeteners, which encompass carbohydrate sweeteners and natural and/or artificial calorie-free/low-calorie sweeteners. In addition, the foods normally comprise them. Typically, the amount of sweeteners used in drinks of the invention depends on the intensity of sweetness of the individual sweeteners. The amount of calorie-free/low-calorie sweeteners varies depending on the intensity of sweetness of each sweetener.

The foods of the invention may be sweetened by any carbohydrate sugars, preferably by monosaccharides and/or disaccharides. Typically, the sweetened drinks contain about 0.1 to about 20% of sweeteners, most preferably, about 6 to about 14%. These sugars may be contained in solid or liquid form, typically, preferably added as syrup, most preferably as concentrated syrup such as high fructose corn syrup. In order to prepare the drinks of the invention, these sugar sweeteners may be provided, to a certain level, in the form of fruit juice and/or other ingredients for drinks such as flavors.

EXAMPLES

Example 1

Effects on Suppression of Gastritis

The six-week old Mongolian gerbils were given drinking water with 10 ppm of MNU (a carcinogen N-methylnitrosourea) for one week followed by oral infection with *Helicobacter pylori* ATCC 43504 strain, or were orally infected with $1\times10^8$ CFU of *H. pylori* and 10 ppm of MNU were then given for one week. They were divided into two groups: one was fed with AIN-93G diet for mice containing 0.1% of canolol ("canolol-fed group"); the other was fed with the same diet compositions without canolol. The experiment was continued for up to 52 weeks (X. Cao et al, Jpn. J. Cancer Res., 93, 1293-1298 (2002), N. Shimizu, et al, Cancer Res., 60, 1512-1514 (2000)). Ten gerbils per group were examined.

As a result, pathological study on excised stomach of gerbils fed with the diet containing canolol for 12 weeks revealed that, as shown in FIG. 2, inflammation of gastric epithelium was markedly suppressed in the canolol-fed group (A) in contrast to the group fed with the diet without canolol (B). The result demonstrates that canolol has significant anti-inflammatory activity.

Example 2

Suppression of 8-oxodeoxyguanosine (8-OHdG) Production at the Site of Inflammation by Canolol 8-OHdG is one of the markers of inflammatory disorders that are generated as a result from a reaction of reactive oxygen species with DNA, said reactive oxygen species being derived from inflammatory cells in vivo. The amount of 8-OHdG produced was studied under similar conditions as Example (1) using a conventional fluorescent antibody staining method with the anti-8-OHdG antibody against excised gastric specimens of each group after 12 weeks. As shown in Table 1, while canolol exerted suppressive activity against 8-OHdG production in vivo, it did not show any antibacterial activity. Therefore, it is demonstrated that since canolol exerts suppressive activity against 8-OHdG production, canolol has anti-inflammatory activity, namely suppressive activity against gastritis.

TABLE 1

Effects of canolol on 8-OHdG formation and *Helicobacter pylori* count (CFU) in mid-stomach tissues of Mongolian gerbils infected with *H. pylori*

|  | Amount of 8-OHdG (ratio) | *H. pylori* count (CFU) |
| --- | --- | --- |
| Canolol-fed group | 19.6 ± 5.5* | 4.42 ± 0.2 |
| Control (No canolol) group | 29.8 ± 7.6 | 4.54 ± 0.3 |

*indicates that there was a significant difference P < 0.05

Example 3

Study on Infiltration of Neutrophil and Hyperplasia in Stomach Tissues of Mongolian Gerbils Infected with *H. pylori*.

Specimens of Example (1) were prepared 12 weeks after administration. Stomach specimens were prepared and examined under microscope after conventional hematoxylin-eosin staining. The results are shown in Table 2.

TABLE 2

Infiltration of neutrophils and hyperplasia in the stomach tissues
of gerbils infected with *H. pylori* from each group

| Tested group (n = 10, each) | Neutrophil infiltration | | Hyperplasia | |
|---|---|---|---|---|
| | Gastric antrum | Gastric corpus | Gastric antrum | Gastric corpus |
| Canolol fed group | 1.2 ± 0.4* | 0.9 ± 0.2* | 1.2 ± 0.6* | 0.7 ± 0.2* |
| No canolol | 2.9 ± 0.3 | 1.5 ± 0.1 | 2.2 ± 0.3 | 1.2 ± 0.1 |

*indicates that there was a significant difference (P < 0.01)

As shown in Table 2, the canolol-fed group significantly suppressed gastritis in both gastric antrum and corpus.

Example 4

Quantification of Induction of cycloxygenase-2 (COX-2) and Enzyme Activity of the Inducible Form of NO Synthase (iNOS) in Gastric Lesions Infected with *H. pylori*

The expression levels of both enzymes were quantified by means of enzyme antibody using the specimens of Example (1) prepared 12 weeks after administration according to Example (2). Both COX-2 and iNOS induced during inflammation are typical enzymes to onset an inflammation reaction. Namely, COX-2 produces prostanoid inflammatory mediators such as prostaglandin $E_2$, and iNOS produces nitric oxide (NO), where these mediators and NO evokes inflammation. Both superoxide ($O_2^-$) and NO produced at the site of inflammation immediately react with each other and form more reactive peroxynitrite ($ONOO^-$) (described later).

Figure 3B:
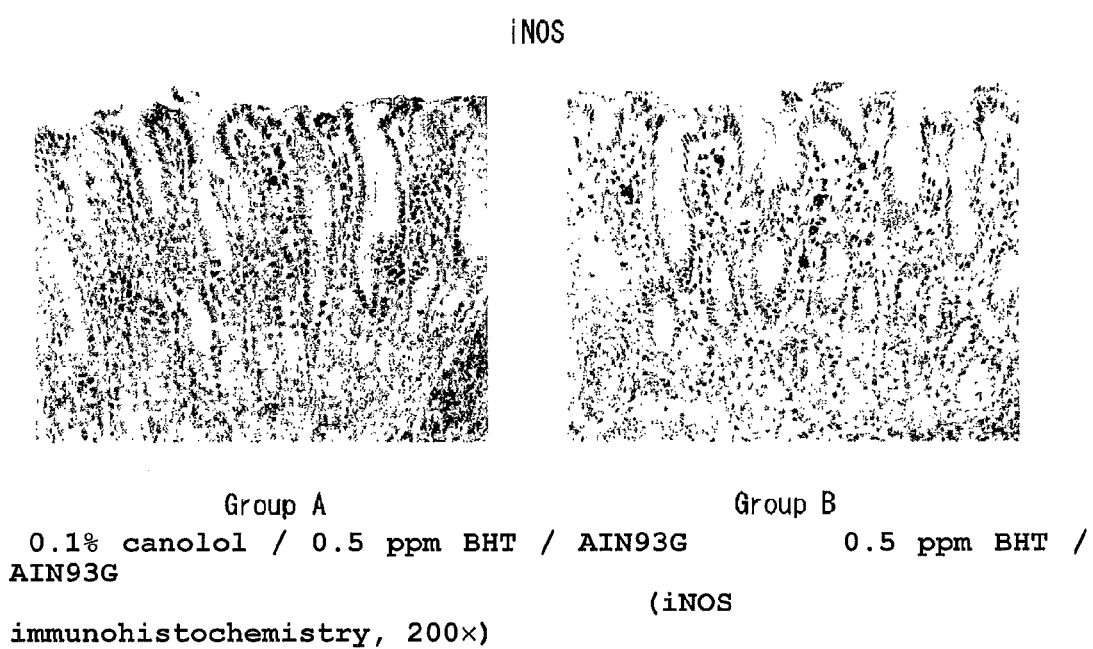
FIG. 3B shows pathological findings of iNOS after immunostaining.

FIG. 3A shows pathological findings after immunostaining of COX-2, and FIG. 3B shows pathological findings after immunostaining of iNOS. Table 3 shows quantification of both enzymes from immunostaining using respective antibodies.

TABLE 3

Induction of inflammatory enzymes and suppression
by canolol diet in *H. pylori* infected model

| Test group | Gastric antrum | | Gastric corpus | |
|---|---|---|---|---|
| | COX-2 | iNOS | COX-2 | iNOS |
| Canolol-fed group (n = 10) | 0.9 ± 0.2* | 0.9 ± 0.1* | 0.6 ± 0.2* | 0.5 ± 0.1* |
| Control group (no canolol) (n = 10) | 2.2 ± 0.2 | 1.7 ± 0.2 | 1.0 ± 0.2 | 0.8 ± 0.2 |

*indicates that there was a significant difference between two groups (P < 0.001)

Example 5

Suppression of NO Production from Macrophages by Canolol

Next, the inflammatorily exuded peritoneal macrophages were treated with bacterial (*E. coli*) lipopolysaccharide (LPS) (1 µg/ml) and interferon-γ (0.1 µg/ml) in vitro, then the amount of NO, the inflammatory mediator released from the macrophages, was quantified as $NO_3^- + NO_2^-$ by a conventional method (Gries method) [Stuehr D J, et al, J. Exp. Med., 169, 1543-55 (1989)] (FIG. 4). That is, to the 6-week old female BALB/c mice (SPF), 10% proteose peptone (1 ml) was injected intraperitoneally. The exuded peritoneal macrophages were collected by peritoneal puncture using a needled syringe, centrifuged in the presence of 10% heat-inactivated fetal calf serum and washed. The peritoneal macrophages ($1 \times 10^5$/well), LPS (1 µg/ml), interferon-γ (IFN-γ) (0.1 µg/ml) and variable doses of canolol (5, 12.5, 25, 50, 100 µM) were plated in the plastic microplate (96-well) (Sumitomo Bakelite, Cat. #MS-8096F), and allowed to incubate for 24 hours at 37° C., under 5% $CO_2$ and 95% air. Then, nitrite and nitrate ions in the supernatant were quantified by the Gries method. The results are shown in FIG. 4. The culture medium used for the macrophages was RPMI-1640 containing 10% of heat-inactivated fetal calf serum. As control groups, LPS alone, and LPS+IFN-γ without canolol were used. The vertical axis of FIG. 4 indicates the total amount of nitrate and nitrite ions.

When the effects of canolol on the survival of macrophage were examined, canolol was found to be essentially non-toxic at 100 µM (FIG. 5) where the effective concentration of canolol was 10-100 µM. Canolol at 800 µM or higher was found cytotoxic, while the effective concentration of 100 µM or less shows no cytotoxicity, thus canolol is suitable for use as medicament.

Example 6

Neutralizing Capacity of Canolol Against the Toxicity by Peroxynitrite

At the inflammatory site, peroxynitrite ($ONOO^-$) is excessively generated as a result of inflammatory reaction, and toxic effect thereof to living cells is one of the cause of pathogenesis. It was anticipated that canolol would exert protective effects against said toxicity of $ONOO^-$ to cultured cells. To demonstrate this, two cell lines, human bronchial epithelial cell (MBE 140), and human embryonic kidney epithelial cell (HEK 293) were tested at $1 \times 10^5$ cells/well respectively, by exposing with a peroxynitrite liberating agent, SIN-1 [(3-(4-morpholinyl) sydnonimine HCl] obtained from Dojin Chemical Laboratory, Kumamoto, Japan (at 100 µM), either with canolol (5, 12.5, 25, 50 100 µM) or without canolol (control) in the 96-well microplate. The cell survival was quantified by using the MTT method. The results are shown in FIG. 6. A half-life of SIN-1 in the culture medium was 6 hour.

As shown in FIG. 6 it was found that the anti-inflammatory agent of the invention significantly neutralized the toxicity of $ONOO^-$ against human embryonic kidney epithelial cells HEK 293 at 12.5-50 µM.

Example 7

Suppression of Gastric Carcinogenesis in Mongolian Gerbils Infected with *Helicobacter pylori* and Treated with Chemical Carcinogen N-methylnitrosourea (MNU)

In accordance with Examples (1)-(4), gerbils were bred for more than 20 weeks, and at around 57 weeks, stomach was excised from gerbils under anesthesia and fixed, and paraffin blocks thereof were prepared by a conventional method. Thin slices obtained from the paraffin blocks were examined with HE (hematoxyline eosin) staining under microscope. Those identified as carcinoma were calculated for each gerbil, and the results are shown in Table 4. With regard to gerbils fed with 0.1% canolol, the cancer incidence of was 15% while that of gerbils without canolol was 41%. This means that 64% suppression of the cancer incidence was observed. These results are consistent with the data of genetic damage by ONOO⁻ as seen in mutagenicity, by peroxynitrite (ONOO⁻) of *Salmonella* as in FIG. 6, being suppressed by canolol.

TABLE 4

Suppression of carcinogenesis by canolol [a]

| Experimental Group | No. of gerbils/ group | Treatment | Incidence of carcinoma | | | |
|---|---|---|---|---|---|---|
| | | | Differentiation | Undifferentiation | Frequency (%) | Rate of suppression (%) |
| G | 40 | Hp + MNU →Canolol + BHT | 5 | 1 | 6/40 (15.0) | 64.0 |
| H | 33 | Hp + MNU → BHT | 11 | 2 | 13/33 (39.4) | 6.5 |
| I | 36 | Hp + MNU | 15 | 0 | 15/36 (41.7) | 0 |
| J | 5 | Broth → Canolol + BHT | 0 | 0 | 0/5 (0) | — |

[a] After oral infection with *H. pylori*, gerbils received drinking water with 10 ppm of MNU. One week after MNU water, the 0.1% canolol diet was started. The table shows the quantified pathological findings of the stomach of Mongolian gerbils dissected after 57 weeks.

Example 8

Figure 7B:
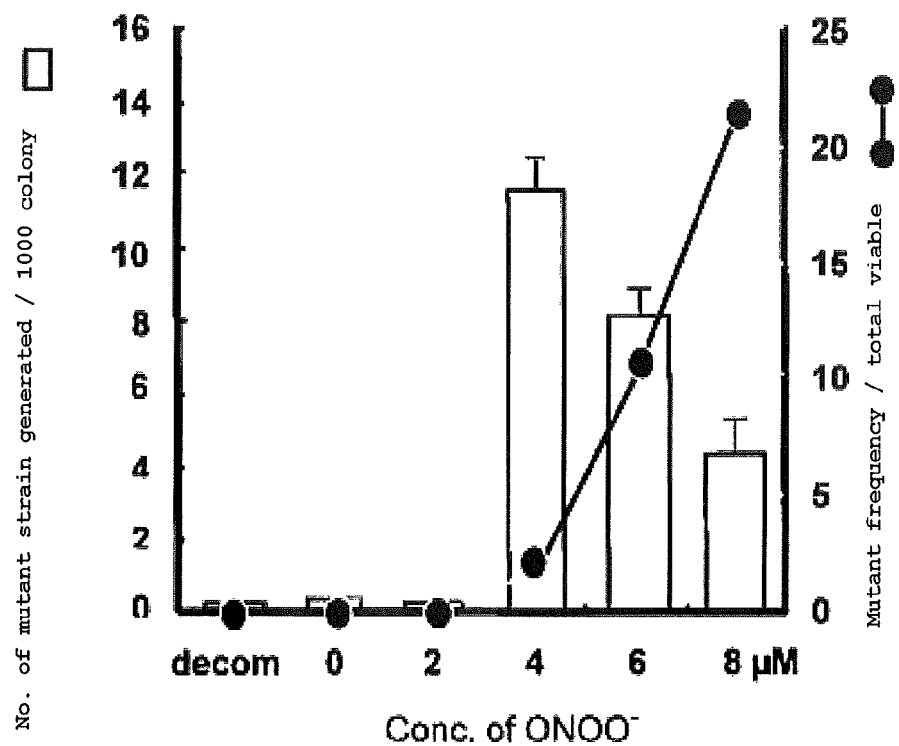
FIG. 7B shows mutant colonies.
Figure 7C:
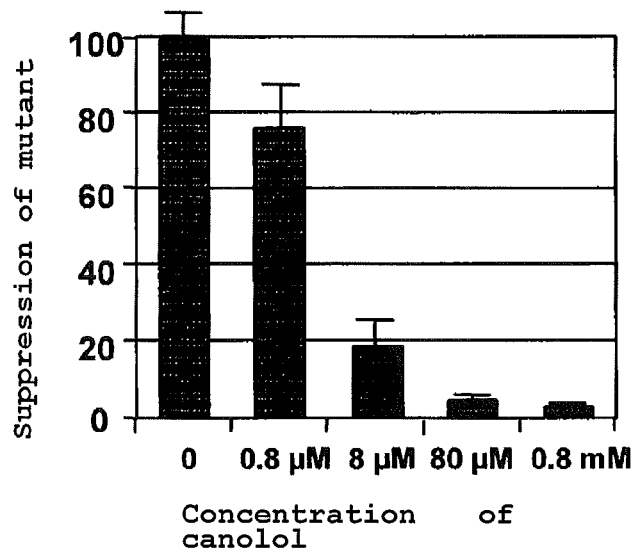
FIG. 7C shows suppression of mutant generation by treatment of the cancer-preventive agent of the invention.

$1 \times 10^8$ CFU of *Salmonella typhimurium* TA102 was taken into a beaker under sterile condition, then ONOO⁻ was continuously infused under stirring to make a predetermined concentration of ONOO⁻ between 1-800 μM. (FIG. 7A). An aliquot of *S. typhimurium* at each time point was removed to a petri dish containing modified Ames medium which permits selective growth of only mutant strains, and was cultured. FIG. 7B shows the data of resultant mutant colonies. The mutant colonies were formed progressively at or above 4 μM of ONOO⁻, while they were not formed with addition of 8 μM canolol. Namely, it was demonstrated that DNA damage caused by ONOO⁻, thereby mutant colony formation could be suppressed by canolol, and that would lead to cancer prevention.

Aforementioned results demonstrate that canolol can be a cancer-preventive agent in vivo and in vitro.

A series of these experiments clarified that canolol exhibits protective effects on the cytotoxicity of ONOO⁻. Therefore, compositions containing canolol can be used as anti-inflammatory agents and cancer-preventive agents.

Accordingly, canolol can be used as a component of cosmetics and foods as well as in medicine as an anti-inflammatory agent and cancer-preventive agent by administering to the host. Followings are the representative formulations for medicament, cosmetic and food containing canolol.

Example 9

Cream Medicament: Anti-Inflammatory Cream Containing Canolol (Ointment)

To conventional fat (plant or animal), lanolin, vaseline, coconut oil, palm oil, camellia oil, other hydrogenated vegetable oil, glycerin or the mixture thereof, a conventional antioxidant such as BHT (2,6-di-tert-butyl-4-methylphenol, butylated hydroxytoluene), or a-tocopherol, or vitamin C, carotenoids or derivative thereof is added with 0.001-0.1%, more preferably 0.01%, and canolol content of 0.01-5%, more preferably 0.3-3.0% is added thereto. The cream thus obtained is applied and rubbed to lesions such as skin. Various emulsifiers such as sugar esters or lecithin as well as antiseptics may be added to the cream at an appropriate amount.

Example 10

To 10 ml of aqueous solution containing canolol-containing emulsified liquid or solution formulation and a small amount of antioxidant (for example, palmityl ascorbate derivative(s), or PD thereof, BHT etc.), 0.1-10 g canolol dissolved in 10 ml of ethanol, propanol or isopropanol was added to prepare a drug solution. Humidification and/or sonication may be applied. Alcohol or aqueous solution may contain 0.1-50% of canolol.

Example 11

Lipid Formulation (Capsulated Lipid Formulation)

Lipid formulation can be prepared by dissolving canolol in soybean oil, sesame seed oil, rape seed (canola) oil, olive oil, medium-chain fatty acids, linoleic acid, camellia oil, poppy seed oil or coconut oil to make the content of 0.1-50%. The lipid formulation may be filled in soft gel capsules or the like to contain 0.1-0.5 g of canolol per capsule. One to ten capsules may be orally administered as an anti-inflammatory agent per day.

Example 12

Tablet Formulation

Canolol may be administered as canolol-containing tablets. To one or more conventional materials described in Japanese Pharmacopoeia such as lactose, maltose, various starches, cellulose, chitin, chitosan, hemicellulose, polyvinyl alcohol, polyethylene glycol and calcium phosphate, ethanol containing 0.01-0.1% of the aforementioned general antioxidant such as BHT dissolving 1-50% of canolol therein, or canolol itself is added, stirred thoroughly, then ethanol is removed under vacuum, then form tablets. One tablet may contain 1-500 mg. For therapeutic or preventive use, 3-5 tablets may be administered for 3 times a day after each meal.

Example 13

Aqueous Formulation for Injection 100 ml of canolol may be dissolved in 1 ml of alcohol (ethanol), and the resultant is added to 50-100 times its volumes of distilled water, physiological saline, 5% glucose, 8% sodium bicarbonate solution, mannitol solution, lactose solution, or hyperalimentation reinfusion such as Intralipid®, vitamin mixture solution, and infusion such as amino acid solution, or other reinfusion to prepare injection solution. Canolol can also be made into micelle formulation using various micelle forming agents or cyclodextrin inclusions, or emulsified suspension by adding lecithin, sphingomyelin or sugar esters such as Nikkor®. It can also be directly added to high calorie reinfusion such as Intralipid® or aqueous injection.

Concentration of canolol may be 1-300 mg per ml, more preferably 50-80 mg/ml for injection formulation.

Example 14

Suppository Formulation

In accordance with the above examples, with cholesterol, lanoline, vaseline, palm oil or various solid fats that melt or soften at about 37° C., canolol containing formulation in shape of a conventional rectal suppository is prepared and used as enteric formulation.

Example 15

Cosmetics are prepared by using appropriate excipient, fragrance, coloring agent and other active ingredients in appropriate forms.

Example 16

Various foods, beverages, vitamin drinks, biscuits or the like containing 0.01-2.0% of canolol in addition to antioxidant BHT or vitamin C may be prepared. By taking these foods cancer can be prevented. That is, said foods can be used as cancer-preventive agents.

Industrial Applicability

The anti-inflammatory agent and cancer-preventive agent according to the invention, or medicament, cosmetic or food comprising the same not only provide sufficient anti-inflammatory and cancer preventing activity but also exert superior effects in terms of manufacture, manufacturing cost, bioactivity, safety, administration and intake compared to conventional agents. The present invention therefore contributes to pharmaceutical industry, cosmetics industry, food industry and related industries to a great extent.

What is claimed:

1. A method for treating inflammation caused by infection with *Helicobacter pylori* in a subject comprising administering to the subject an anti-inflammatory agent comprising 4-vinyl-2,6-dimethoxyphenol.

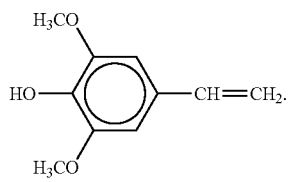

[Chemical formula 1]

2. The method according to claim 1 wherein the inflammation is from one or more diseases selected from the group consisting of gastro-duodenitis, gastritis and colitis.

3. The method according to claim 1, wherein inflammation is suppressed by inhibition of COX-2 activity, inhibition of cytokine induction or any combination thereof.

4. The method according to claim 1, wherein the anti-inflammatory agent further comprises an excipient for medicament.

5. The method according to claim 1, wherein the anti-inflammatory agent further comprises a cosmetic ingredient.

6. The method according to claim 1 wherein the anti-inflammatory agent is in the form of a cream, tablet, capsule, lipid formulation, aqueous formulation (water solubilized form) or emulsion.

7. The method according to claim 1, wherein the anti-inflammatory agent further comprises a food ingredient.

* * * * *